United States Patent
Patat et al.

(10) Patent No.: US 6,426,222 B1
(45) Date of Patent: Jul. 30, 2002

(54) METHOD FOR INDUCING OSTEOBLAST DIFFERENTIATION OF HUMAN EXTRAMEDULLARY ADIPOSE TISSUE CELLS

(75) Inventors: Jean-Louis Patat, Paris; Jean Darondel, Cambremer; Jean-Pierre Ouhayoun; Alain Francis LeCoeur, both of Paris, all of (FR)

(73) Assignee: Bio Holdings International Limited, Tortola (VG)

( * ) Notice: Subject to any disclaimer, the term of this patent is extended or adjusted under 35 U.S.C. 154(b) by 0 days.

(21) Appl. No.: 09/530,939
(22) PCT Filed: Nov. 16, 1998
(86) PCT No.: PCT/FR98/02438
§ 371 (c)(1), (2), (4) Date: May 10, 2000
(87) PCT Pub. No.: WO99/25813
PCT Pub. Date: May 27, 1999

(30) Foreign Application Priority Data

Nov. 14, 1997 (FR) .............................. 97 14328

(51) Int. Cl.$^7$ .................................. C12N 5/08
(52) U.S. Cl. .................. 435/377; 435/375; 435/325; 435/366; 435/372; 424/93.7
(58) Field of Search .................. 435/375, 377, 435/383, 385, 384, 395

(56) References Cited

U.S. PATENT DOCUMENTS 5,279,831 A * 1/1994 Constantz et al.
5,370,692 A * 12/1994 Fink et al.
5,532,226 A * 7/1996 Demarest et al.

FOREIGN PATENT DOCUMENTS

WO 97 18842 5/1997
WO WO-97/26326 A1 * 7/1997

OTHER PUBLICATIONS

Rickard et al., "Induction of Rapid Osteoblast Differentiation in Rat Bone Marrow Stromal Cell Cultures by Dexamethasone and BMP–2," Developmental Biology, Jan. 1994, 161:218–228.*
Grigoriadis et al., "Differentiation of muscle, fat, cartilage, and bone from progenitor cells present in a bone derived clonal cell population: effect of dexamethasone," J Cell Biology, 1988, (6):2139–2151.*
Le Coeur et al, "In vitro induction of osteogenic differentiation from non–osteogenic mesenchymal cells," Biomaterials, vol. 18, Jul. 1997, pp. 989–993.
Hauner et al, "Promoting effect of glucocorticoids on the differentiation of human adipocyte precursor cells cultured in a chemically defined medium," J. Clinical Investigation, vol. 84, pp. 1663–1670.

* cited by examiner

Primary Examiner—Leon B. Lankford, Jr.
Assistant Examiner—Ruth A. Davis
(74) Attorney, Agent, or Firm—Dennison, Schultz & Dougherty

(57) ABSTRACT

A method for inducing osteoblast differentiation and/or for obtaining cells engaged in osteoblast differentiation, starting from human extramedullary adipose tissue cells, comprising the step consisting in incubating said starting cells in a liquid nutrient medium for a period of time sufficient to enable said cells to develop, said nutrient medium containing a solution of at least one glucocorticoid and being free from adipogenic factor. Applicable to making bone implants, in particular using autologous cells.

27 Claims, No Drawings

METHOD FOR INDUCING OSTEOBLAST DIFFERENTIATION OF HUMAN EXTRAMEDULLARY ADIPOSE TISSUE CELLS

This application is a national phase filing under 35 USC 371 of PCT/FR98/02438.

BACKGROUND OF THE INVENTION

The invention relates to a method of obtaining cells of osteoblast phenotype from cells present in human extramedullary adipose tissue. The resulting cells can be used for making bone implants.

It is known that in order to remedy losses of bone tissue following injury or surgical operations, it is possible to implant replacement or filler materials. These materials can be bone grafts or artificial products such as porous ceramics, or else natural products such as coral skeleton.

The making of allografts comprises in particular risks of transmitting certain serious viral diseases. The making of autografts is more satisfactory from this point of view, but taking the graft requires surgical intervention, which presents considerable risks of morbidity.

For these reasons, it has been recommended to use implants based on biocompatible, and possibly biodegradable materials, such as tricalcium phosphate, hydroxyapatite, plaster, coral, polymers based on poly(lactic acid), etc. Macroporous materials are particularly advantageous since the presence of pores enhances bone regrowth.

For several years, research has been directed towards using cells having osteogenic potential, optionally in combination with biomaterials; see for example French patent No. 2 679 250 which contemplates culturing osteoblasts on a porous three-dimensional solid support constituted by coral skeleton for the purpose of being implanted in patients suffering from a loss of bone substance, that has already occurred or that is expected (when surgical resection is planned).

The interest of such methods naturally lies in enabling implants to be made using autologous cells.

In this field, research has been directed towards using bone marrow cells which are capable of differentiating into osteoblasts, in particular under the influence of certain growth factors that have an osteoinducing effect. It is indeed known that bone marrow cell cultures are capable of tending in particular towards development of osteoblast phenotypes.

However, taking bone marrow presents the same drawbacks as taking bone grafts.

Studies performed on the rabbit have shown that cells of the stroma-vascular compartment of extramedullary adipose tissue are capable of differentiating into osteoblasts in in vitro cultures in the presence of the BMP2 osteo-inducing factor and dexamethasone; see L. Lecoeur et al., Cellular Engineering, Vol. 2, No. 2, 1–7 (1997). Dexamethasone on its own does not make this differentiation possible.

SUMMARY OF THE INVENTION

It has now been discovered that, on the contrary, in vitro culturing of certain human extramedullary adipose tissue cells can lead to osteoblast differentiation in the presence of a glucocorticoid on its own, e.g. in the presence of dexamethasone on its own, i.e. not associated with an osteo-inducing factor. The use of such factors, which are expensive products, is not necessary.

Of the various osteo-inducing factors, mention can be made of the protein mediator known as "bone morphogenetic protein" (BMP), described by M.R. Urist et al., P.N.A.S. USA 76: 1828–1832 (1979). That terminology covers in fact various osteo-inducing protein factors (from BMP2 to BMP9), see for example Yamaguchi et al., Sem. Cell. Biol. 6, 165–173 (1993).

The invention thus provides a method for inducing osteoblast differentiation and/or for obtaining cells engaged in said differentiation, starting from human extramedullary adipose tissue cells, the method comprising the step consisting in incubating said starting cells in a liquid nutrient medium for a period of time sufficient to enable said cells to develop, said nutrient medium containing a solution of at least one glucocorticoid and being free from adipogenic factor, and in particular free from insulin.

In other words, the method of the invention is a method in which starting cells are cultivated and in which at least one glucocorticoid is added to the culture medium in order to induce osteoblast differentiation and/or to obtain cells engaged in said differentiation.

H. Haunder et al. in J. Clin. Invest. 84: 1663–1670 (1998) have described differentiation of human subcutaneous adipose tissue cells into adipocytes by culturing in the presence of insulin and of glucocorticoids.

DETAILED DESCRIPTION OF THE INVENTION

Unlike bone marrow cells, the cells used as starting cells in the method of the invention are cells which are capable of differentiating into adipocytes in the presence of insulin; see in particular J. S. Greenberger, In Vitro, Vol. 15, No. 10, 823–828 (1979).

In the method of the invention, the cells which tend towards osteoblast differentiation are not mature adipocytes which are already differentiated. That is why it is preferred to make use of starting cells selected from collections of cells from which mature adipocytes have been removed. These are stroma-vascular cells which can be obtained in particular by dissociating the adipose tissue by using collagenase, and then removing the mature adipocytes, e.g. by centrifuging. Mature adipocytes are in fact of lower density than the other cells present in the starting adipose tissue, so they can be removed by centrifuging.

In practice, it is possible to use as starting cells cells which are capable of adhering to polystyrene surfaces, e.g. after adipose tissue has been dissociated by a collagenase and mature adipocytes have been removed.

The cells are incubated in the culture medium under standard conditions that enable them to develop, i.e. not only to survive but also to proliferate and/or differentiate. Standard conditions for culturing human cells are known: e.g. a temperature of about 37° C.; an atmosphere having an air-$CO_2$ ratio of 95:5; and a pH close to neutral.

The culture medium used is a conventional liquid nutrient medium containing the ingredients necessary for mammal cell development. These ingredients are known. They are mainly inorganic salts (in particular Na, K, Mg, Ca, and possibly Cu, Fe, and Zn), amino acids, vitamins, and sources of carbon (e.g. glucose). Specifically, it is possible to use a nutrient medium such as the minimum essential medium MEM from EAGLE, supplemented with fetal calf serum or preferably autologous human serum.

It is also possible to use nutrient media that are more elaborate, of the DME type (the EAGLE medium as modified by DULBECCO), possibly mixed with the F12 medium from HAM, with or without serum, and preferably in the presence of autologous serum.

Osteo-inducing factors such as BMP factors can be added to these culture media, but as mentioned above, these factors are not necessary for inducing osteoblast differentiation of the human cells used in the method of the invention. On the basis of the results obtained in the experimental part below, the presence of an osteo-inducing factor can even have an unfavourable effect (at least in some cases). It is thus possible to use media that are free from osteo-inducing factors.

The culture media used preferably have bone-promotor factors added thereto such as ascorbic acid and beta-glycerophosphates (e.g. of sodium or calcium).

Furthermore, the culture media used in the method of the invention are free from adipogenic factors, and in particular they are free from insulin. In this context, it should be observed that glucocorticoids have an adipogenic effect on cells of the stroma-vascular fraction of extramedullary adipose tissue only in the presence of insulin; see Hauner et al., in the above-cited article.

It is possible to perform culturing in conventional culture dishes. It is also possible to perform culturing on a biocompatible three-dimensional solid support immersed in the liquid culture medium.

The cells can be incubated with the glucocorticoid either from the beginning of culturing, immediately after inoculation, or else subsequently, e.g. after the cells have reached confluence, or at any moment between those two events.

Suitable glucocorticoids are those which make it possible, after the cells have been incubated for a sufficient period of time in the presence of the glucocorticoid under study, to obtain cultures containing cells engaged in osteoblast differentiation.

In the present application, it is considered that cells are engaged in osteoblast differentiation when they satisfy at least the first two of the following conditions:
  production of alkaline phosphatase of the bone-liver-kidney type;
  production of type I collagen; and
  production of osteocalcine.

Such cells, which are also referred to as "osteoblast phenotype cells", are sufficiently engaged in osteoblast differentiation so that their continued incubation in the nutrient medium and/or implantation makes it possible for at least some of said cells to advance in differentiation all the way to terminal differentiation (with the production of a mineralized extracellular matrix). The characteristic properties of these cells (i.e. alkaline phosphatase production, type I collagen production, and possibly also osteocalcine production) can be demonstrated in conventional manner, e.g. using the tests mentioned in the experimental part below.

At this point it is appropriate to recall that in humans, there exist three isoenzymes of alkaline phosphatase, encoded by three different genes, namely:
  an isoenzyme of bone-liver-kidney type;
  an isoenzyme of placenta type; and
  an isoenzyme of intestine type.

Alkaline phosphatase of bone-liver-kidney type is very sensitive to levamisole.

The concentration of levamisole which gives a 50% inhibition of the activity of bone-liver-kidney type alkaline phosphatase is about 0.03 mM, whereas for the other alkaline phosphatases, 50% inhibition of activity is obtained only with levamisole concentrations of the order of 1 mM for placenta type and of 3 mM for intestine type.

The levamisole inhibition test therefore makes it possible to identify bone-liver-kidney type alkaline phosphatase unambiguously. This test can be performed as follows. 50 microliters of cell extract are taken and is incubated in 100 microliters of a solution containing 1.5 mM 2-amino-2-methyl-1-propanol with a pH of 10.3 and 100 microliters of a 14 mM solution of para-nitrophenol phosphate in the presence of increasing concentrations of levamisole, ranging from $10^{-6}$ M to $10^{-4}$ M. The reaction is performed at 37° C. and it is stopped after 20 minutes by adding 100 microliters of a 0.33 M solution of NaOH. The concentration of levamisole that gives a 50% inhibition can thus be determined.

By means of the tests described in the present application, it is thus possible with routine experiments to determine which natural glucocorticoids or synthetic analogues thereof are suitable, and also the concentrations of glucocorticoid to be used, and the incubation time that suffices for the cells in the presence of the glucocorticoid.

Particular mention can be made of the following glucocorticoids: dexamethasone, hydrocortisone, prednisolone, methylprednisolone, prednisone, triamcinolone, corticosterone, fluocinolone, cortisone, betamethasone, etc.

The incubation time is not less than the time required to obtain cells which satisfy at least the first two above-mentioned conditions. This time is generally about 15 days. To obtain cells that also produce osteocalcine, the duration of the treatment is about 30 days. To obtain cells that are even further advanced in differentiation, and that produce a mineralized extracellular matrix, 35 days to 50 days are generally necessary under the conditions that have been studied.

Glucocorticoid concentrations depend in particular on the nature of the glucocorticoid. These concentrations can be determined in advance in each case by simple routine experiments. In general, concentrations are used of the order of $10^{-5}$ M to $10^{-10}$ M, and in particular of the order of $10^{-6}$ M to $10^8$ M.

The method of the invention can be implemented by performing culturing in conventional culture dishes or on a biocompatible three-dimensional solid support that is porous or non-porous and immersed in a liquid medium. The method can also be implemented by preliminary culturing in conventional culture dishes (possibly in the presence of a glucocorticoid), and then transferring the resulting cells to a three-dimensional solid support immersed in a liquid culture medium.

Before engaging in differentiation, the starting cells generally begin to proliferate, until confluence. During this proliferation stage, it is possible to add a glucocorticoid to the culture medium, which generally has the effect of accelerating the differentiation process. After confluence, if it is observable (for cultures in culture dishes or on a non-porous three-dimensional support), or after a predetermined culturing time (for culturing on a porous three-dimensional solid support) the differentiation stage itself begins, during which the cells are incubated in the presence of a glucocorticoid, which presence is compulsory at this stage.

Cells that have proliferated, or that are being differentiated in culture dishes, can be transferred onto three-dimensional solid supports in order to cause them to multiply and/or continue the differentiation process by incubating the solid support in a liquid nutrient medium containing a glucocorticoid, if necessary. Cells engaged in osteoblast differentiation and obtained in culture dishes can be transferred onto a three-dimensional solid support, e.g. by impregnating said support with a liquid suspension containing said cells. The impregnated supports obtained in this way can be implanted in a human being (in particular in the donor of the adipose tissue used as the starting substance). Such impregnated supports can also be re-cultured by immersing them in a liquid culture medium, possibly in the presence of a glucocorticoid (particularly when the transferred cells still contain non-differentiated cells), prior to being finally implanted.

The three-dimensional solid support must be biocompatible so as to enable it to be implanted in a human. It can be of any suitable shape such as a cylinder, a sphere, a plate, or a part of arbitrary shape.

Of the materials suitable for the biocompatible three-dimensional solid support, particular mention can be made of calcium carbonate, and in particular aragonite, specifically in the form of coral skeleton, porous ceramics based on alumina, on zirconia, on tricalcium phosphate, and/or hydroxyapatite, imitation coral skeleton obtained by hydrothermal exchange enabling calcium carbonate to be transformed into hydroxyapatite (French patent No. 2 223 325), or else apatite-wollastonite glass ceramics, bioactive glass ceramics such as Bioglass™ glasses (Kitsugi et al., J. Biomed. Mater. Res. 21: 1255–1271 (1987), etc.)

Cells engaged in osteoblast transformation can be obtained and/or cultured in accordance with the invention either on the surface of a three-dimensional solid support when the support is not porous, or else both on the surface and in the pores of three-dimensional solids that are porous.

The use of a support based on coral is particularly interesting. It is known that coral can constitute a bone prosthesis that is progressively biodegradable, the recolonization of which by bone during its degradation (see French patent No. 2 460 657, for example) is encouraged by the cells of osteoblast phenotype obtained in accordance with the present invention. Culturing cells on a coral support is described in particular in French patent No. 2 679 250 and in the corresponding U.S. Pat. No. 5,480,827.

The material used as a porous support is preferably a material having pore diameters of from 50 µm to 250 µm, with a porosity generally of from 20% to 80%. This applies in particular to coral of the following genera: *porites, acropora, goniopora, lobophyllia, symphillia,* and *millipora.*

The invention also relates to the use of a glucocorticoid in a liquid culture medium as an additive enabling human cells to develop in culture, said additive being intended to induce osteoblast differentiation in human extramedullary adipose tissue cells cultured in said medium. Naturally, the culture medium is free from any adipogenic factor.

The invention also relates to cells engaged in osteoblast differentiation obtained using the above-described method, the cells satisfying at least the first two of the following conditions:

production of bone-liver-kidney type alkaline phosphatase;

production of type I collagen;

possibly production of osteocalcine; and possibly production of a mineralized extracellular matrix.

These cells can be in the form of a culture lining the pores and/or the surface of a biocompatible threedimensional solid support, as mentioned above.

When they are in the form of cells obtained in conventional culture dishes, they can be used to inoculate such porous and biocompatible three-dimensional solid supports. It is also possible to inoculate such three-dimensional solid supports on which a first layer of cells has already been cultured, such as fibroblasts which can be of autologous origin (see in particular French patent No. 2 679 250), said first layer providing a foundation for the cells of osteoblast phenotype that it is desired to obtain and/or culture.

The cells obtained in accordance with the invention, and in particular in the form of a three-dimensional support impregnated with a suspension containing said cells, can be used to make a bone implant. For this purpose, the cell-filled biocompatible porous three-dimensional supports can be put into place as bone-forming implants. By way of example they can be implanted as pieces for replacing or filling bone tissue and they are progressively colonized by newly formed bone tissue. Such supports can also be implanted in a human, in particular in the donor of the adipose extramedullary tissue cells used as the starting cells, preferably after the three-dimensional porous solid support has been impregnated with an osteo-inducing growth factor in a non-bony site, e.g. in conjunctival tissue, where they give rise to new bone tissue that can subsequently be used as a material for a bone autograft.

The cells engaged in osteoblast differentiation as obtained in accordance with the invention can thus be used to obtain a three-dimensional solid product suitable for serving as a bone implant, as described above. Such use forms a part of the invention.

There follows a description of various experiments that led to the present invention.

Adipose tissue biopsies were taken during plastic surgery of the abdomen on healthy patients, of ages of from 25 to 50.

The tissues taken were sliced thinly into small fragments and digested for 90 minutes with collagenase (2 mg/ml) in a Krebs Ringer buffer at 37° C. Filtering was performed on a screen having a pore size of 100 µm, the filtrate was recovered, and centrifuged at 1000 revolutions per minute (rpm) for 5 min. The supernatant was removed and the pellet was washed several times in Krebs Ringer buffer. The washing and centrifuging steps were repeated several times and on each occasion the supernatant containing mature adipocytes was removed. The resulting cells were suspended in DME/F12 (Sigma Chemical Co., St. Louis, Mo. USA; reference D-6905) culture medium containing 10% fetal calf serum, 100 µg/ml streptomycin, and 100 U/ml penicillin.

Polystyrene culture dishes ("tissue culture flasks" sold by Becton-Dickinson under the references 3013, 3028, and 3084) were inoculated with the resulting cell suspension and incubation was performed at 37° C. under an atmosphere of moist air with 5% additional $CO_2$.

After 12 hours, non-adhering cells were removed by washing with PBS buffer.

Thereafter, adhering cells were cultured in the above-mentioned culture medium, with the medium being changed every 3 days, until confluence.

The cells were then trypsinized and re-inoculated in multiwell dishes at the rate of $2 \times 10^{-4}$ cells/ml in a DME/F12 medium containing 10% fetal calf serum, supplemented with 50 µg/ml ascorbic acid and di-sodium beta-glycerophosphate at a concentration of 10 mM, and containing streptomycin and penicillin at the concentrations mentioned above. Incubation was performed at 37° C.

At confluence, the cells received one of the following treatments:

treatment No. 1: 200 ng/ml of rhBMP2 were added (recombinant human BMP2 supplied by Genetic Institute, Cambridge, Mass., USA);

treatment No. 2: dexamethasone was added up to a concentration of $10^{-7}$ M;

treatment No. 3: 200 ng/ml of rhBMP2+$10^{-7}$ M dexamethasone were added; and untreated controls: incubation in the culture medium (free from rhBMP2 and free from dexamethasone).

Culturing was continued for 30 or more days, with the culture or treatment media being renewed every 3 days.

Treated and non-treated culture samples were analyzed to determine the activity of alkaline phosphatase, the expression of type I collagen, and osteocalcine. In addition, any mineralization of the extracellular matrix was looked for.

Alkaline phosphatase activity was determined by using para-nitrophenol phosphatase as a substrate, using the technique described by L. Lecoeur and J. P. Ouhayoun, Biomaterials 18, 989–993 (1997). The quantity of para-nitrophenol formed upon hydrolysis of the substrate was determined by measuring the absorbance at 410 nm, which was converted into nanomoles of enzyme using a calibration curve established on the basis of known concentrations of para-nitrophenol.

A test was also performed for detecting in situ the activity of alkaline phosphatase on cell cultures fixed with formaldehyde, using a kit for semi-quantitative histochemical detection of alkaline phosphatase (kits sold by Sigma Chemical Co., reference 86R). Alkaline phosphatase activity was visualized on the cell mat by a reddish color.

Levamisole inhibition tests also showed that the alkaline phosphatase produced was of the bone-liver-kidney type.

On cells fixed with formaldehyde, a search was also made for the presence of collagens (of type I and of type II) and of osteocalcine, and also for the presence of any mineralization.

Collagen synthesis was analyzed after 30 days of treatment using the anticollagen antibody (IgG) sold by Southern Biotechnology Associates, USA.

Osteocalcine synthesis was also looked for by means of an anti-osteocalcine antibody (IgG) sold by Biomedical Technologies, Inc., USA.

The antibody determinations were performed with immunofluorescence, with an anti-IgG antibody coupled with fluoresceine being used for development purposes.

The search for possible mineralization of the extracellular matrix was performed by using the von Kossa stain test implemented using the technique described by Cheng et al., Endocrinology 134: 277–285 (1994).

The observed results are described below:

Alkaline phosphatase activity

The cultures treated with rhBMP2 only at a concentration of 200 ng/ml did not present a strong alkaline phosphatase activity. In most cases, this activity was less than or equal to the activity present in the control cultures, even after 35 days of incubation.

In all cases, the highest alkaline phosphatase activities were obtained in the treated cultures subjected to treatment No. 2 and the cultures subjected to treatment No. 3. With treatment No. 2, an activity of not less than 200 nanomoles of para-nitrophenol/30 min/well was observed in nearly all cases, and it was sometimes as high as 700 nanomoles/30 min/well.

Using the cytoenzymatic test, the search for alkaline phosphatase activity observed on cell cultures that had been fixed with formol after 30 days of treatment gave the following results: the cultures subjected to treatment No. 2 or treatment No. 3 had a majority of cells with positive alkaline phosphatase activity. The cells presenting this activity were star-shaped. The cultures subjected to treatment No. 1 presented only a small proportion of cells that were positive for alkaline phosphatase, and those cells were spindle-shaped. In the control cultures, cells expressing alkaline phosphatase activity were rare.

Type I collagen

Culturing performed for 30 days with the culture medium on its own (untreated controls) presented only a weak reaction with the anti-type I collagen antibody. The cultures subjected to treatment No. 1 also reacted little with that antibody. The cultures subjected to treatment No. 2 developed highly fluorescent nodular structures. Treatment No. 3 did not induce such structures, and only a small amount of fluorescence was observed, localized in a few groups of cells.

Type II collagen

After 30 days, the treated cultures presented only a weak fluorescent marking, just like the control cultures.

Osteocalcine

The control cultures and the cultures subjected to treatment No. 1 responded very weakly to the anti-osteocalcine antibody. The cultures subjected to treatment No. 3 had certain zones in which marking was slightly more intense. The strongest reaction was obtained using the cultures treated with dexamethasone on its own. The nodular structures induced in these cultures presented a very high level of fluorescent marking. However, the surrounding cellular mat was not marked and osteocalcine synthesis appeared to be restricted to the nodular structures.

Examination of the cells under a scanning electron microscope

The control cells incubated with the culture medium on its own were of uniform appearance, and quite massive in shape. The cells subjected to treatment No. 1 were more elongate in shape. The cultures subjected to treatment No. 3 developed cells of more heterogeneous appearance and irregular shape. For the cultures subjected to treatment No. 2, the scanning electron microscope showed the presence of nodular structures.

In vitro mineralization

After 30 days, cultures whether treated or untreated did not develop a mineralized extracellular matrix.

After 45 days, only very few points of mineralization were to be observed on the untreated cells. With the cells subjected to treatment No. 1 or treatment No. 3, no points of mineralization would be detected. On the cultures subjected to treatment No. 2, numerous centers of mineralization were observed, including mineralized nodules.

What is claimed is:

1. A method for obtaining cells engaged in osteoblast differentiation starting from human extramedullary adipose tissue cells, which comprises incubating said tissue cells in a liquid nutrient medium free from adipogenic factor and comprising at least one glucocorticoid as sole component necessary for the engagement of said cells in osteoblast differentiation.

2. The method according to claim 1, wherein said nutrient medium is free from insulin.

3. The method according to claim 1, wherein said tissue cells are separated from mature adipocytes.

4. The method according to claim 1, wherein said tissue cells adhere to a polystyrene surface.

5. The method according to claim 1, wherein the incubated cells produce bone-liver-kidney alkaline phosphatase and type I collagen.

6. The method of claim 5, wherein the incubated cells further produce at least one of osteocalcine and a mineralized extracellular matrix.

7. The method according to claim 1, wherein the glucocorticoid is selected from the group consisting of dexamethasone, hydrocortisone, prednisolone, methylprednisolone, prednisone, triamcinolone, corticosterone, fluocinolone, cortisone, and betamethasone.

8. The method according to claim 1, further comprising impregnating the tissue cells on a biocompatible three-dimensional solid support prior to incubation.

9. The method according to claim 8, wherein the three-dimensional solid support is made of a material selected from the group consisting of calcium carbonate, hydroxyapatite, calcium carbonate surface-coated with hydroxyapatite, ceramics and mixtures thereof.

10. The method according to claim 1, which further comprises recovering the incubated cells engaged in osteoblast differentiation and impregnating a biocompatible three-dimensional solid support with a suspension of the recovered cells.

11. The method according to claim 10, further comprising incubating the impregnated support.

12. The method according to claim 10, wherein the three-dimensional solid support is made of a material selected from the group consisting of calcium carbonate, hydroxyapatite, calcium carbonate surface-coated with hydroxyapatite, ceramics and mixtures thereof.

13. The method of claim 1, wherein the tissue cells are incubated at a temperature of about 37° C., a pH of about 7, and under an atmosphere having an air-$CO_2$ ratio of about 95:5.

14. A method for obtaining cells engaged in osteoblast differentiation starting from human extramedullary adipose tissue cells, which comprises incubating said tissue cells in a liquid nutrient medium free from adipogenic factor and from protein having an osteo-inducing effect, said medium comprising at least one glucocorticoid as sole component for the engagement of said cells in osteoblast differentiation.

15. The method according to claim 14, wherein the nutrient medium is free from bone morphogenetic protein (BMP).

16. The method according to claim 14, wherein said nutrient medium is free from insulin.

17. The method according to claim 14, wherein said tissue cells are separated from mature adipocytes.

18. The method according to claim 14, wherein said tissue cells adhere to a polystyrene surface.

19. The method according to claim 14, wherein the incubated cells produce bone-liver-kidney alkaline phosphatase and type I collagen.

20. The method of claim 19, wherein the incubated cells further produce at least one of osteocalcine and a mineralized extracellular matrix.

21. The method according to claim 14, wherein the glucocorticoid is selected from the group consisting of dexamethasone, hydrocortisone, prednisolone, methylprednisolone, prednisone, triamcinolone, corticosterone, fluocinolone, cortisone, and betamethasone.

22. The method according to claim 14, wherein the tissue cells are impregnated on a biocompatible three-dimensional solid support prior to incubation.

23. The method according to claim 22, wherein the three-dimensional solid support is made of a material selected from the group consisting of calcium carbonate, hydroxyapatite, calcium carbonate surface-coated with hydroxyapatite, ceramics and mixtures thereof.

24. The method according to claim 14, which further comprises recovering the incubated cells engaged in osteoblast differentiation and impregnating a biocompatible three-dimensional solid support with a suspension of the recovered cells.

25. The method according to claim 24, which further comprises incubating the impregnated support.

26. The method according to claim 24, wherein the three-dimensional solid support is made of a material selected from the group consisting of calcium carbonate, hydroxyapatite, calcium carbonate surface-coated with hydroxyapatite, ceramics and mixtures thereof.

27. The method of claim 14, wherein the tissue cells are incubated at a temperature of about 37° C., a pH of about 7, and under an atmosphere having an air-$CO_2$ ratio of about 95:5.

* * * * *